(12) United States Patent
Harding et al.

(10) Patent No.: US 8,377,010 B2
(45) Date of Patent: Feb. 19, 2013

(54) MEDICAL ACCESS DEVICE

(75) Inventors: Weston F. Harding, Lehi, UT (US); Glade H. Howell, Sandy, UT (US); Craig N. Gawreluk, Park City, UT (US); Kelly David Christensen, Centerville, UT (US); Marty Lee Stout, South Weber, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 581 days.

(21) Appl. No.: 11/281,574

(22) Filed: Nov. 17, 2005

(65) Prior Publication Data

US 2007/0112311 A1    May 17, 2007

(51) Int. Cl.
*A61M 5/00* (2006.01)
(52) U.S. Cl. ........................... 604/246; 604/247
(58) Field of Classification Search .................. 604/247, 604/246, 256
See application file for complete search history.

(56) References Cited

U.S. PATENT DOCUMENTS

| | | | | |
|---|---|---|---|---|
| 5,399,168 | A | * | 3/1995 | Wadsworth et al. ........... 604/175 |
| 5,632,735 | A | * | 5/1997 | Wyatt et al. .................... 604/539 |
| 5,807,350 | A | * | 9/1998 | Diaz .............................. 604/256 |
| 6,908,459 | B2 | * | 6/2005 | Harding et al. ................ 604/533 |
| 2004/0199126 | A1 | * | 10/2004 | Harding et al. ................ 604/256 |

\* cited by examiner

*Primary Examiner* — Laura Bouchelle
(74) *Attorney, Agent, or Firm* — Kinney & Lange, P.A.

(57) ABSTRACT

A medical access device provides needleless access to patient fluid lines such as intravascular catheters. A retaining ring at the top end of the housing of the medical access device is molded around a septum that provides access for a tubular portion of a medical device such as a male luer taper of a syringe. Alternatively, the retaining ring may also be molded around the body or around both the body and the base of the housing. The molded retaining ring and septum are attached by mechanical attachment and/or chemical adhesion to minimize axial and rotational movement between the septum and the housing.

11 Claims, 17 Drawing Sheets

MEDICAL ACCESS DEVICE

BACKGROUND OF THE INVENTION

The present invention relates to a connector for accessing patient fluid lines. In particular, the present invention is an access connector that may be opened by a tubular portion of a medical device, such as a male luer taper of a syringe.

In the course of treating patients, clinicians are continually transferring patient fluids between various containers and intravascular (IV) lines or through IV catheters. Transfer of these fluids is preferably through a closed system to prevent microbes from entering the system and causing infections in the patients. Many of these closed systems have relied on the use of a needle to penetrate a rubber or silicone septum to gain access to the fluid lines. The clinician may then inject fluid into or withdraw fluid from the patient via a needle and syringe. The septum then reseals after the needle is withdrawn, which prevents backflow of the fluids and closes the system once again.

Because of the concern over accidental puncture with needles contaminated with a patient's blood or other fluids, needleless mechanisms have been developed to access patient fluid lines. One such mechanism utilizes a silicone septum that has a slit in it wide enough to allow a standard male luer taper to access the fluids. In this type of mechanism, the silicone septum is encompassed by a thermoplastic housing. With current connectors, the septum is bonded to the housing with adhesive.

Bonding between the septum and housing prevents the septum from rotating within the housing while a male luerlock taper is locked and unlocked from the connector. In addition, as a male luer taper is drawn out of the septum, the taper tends to stick to the septum and stretches the septum out of the housing. If the septum is not bonded to the housing, the septum will pull out, or, as the taper slips off the septum, the septum snaps back into the housing causing fluids to spatter.

BRIEF SUMMARY OF THE INVENTION

The present invention is an access connector for accessing patient fluid lines. The access connector includes a retaining ring, a housing, and a septum. The retaining ring is molded around the septum, which has been inserted into a channel formed in the housing. The septum provides resealable access to the fluid line. The present invention minimizes axial and rotational movement between the housing and the septum to allow optimum performance by the connector.

DETAILED DESCRIPTION

Figure 1:
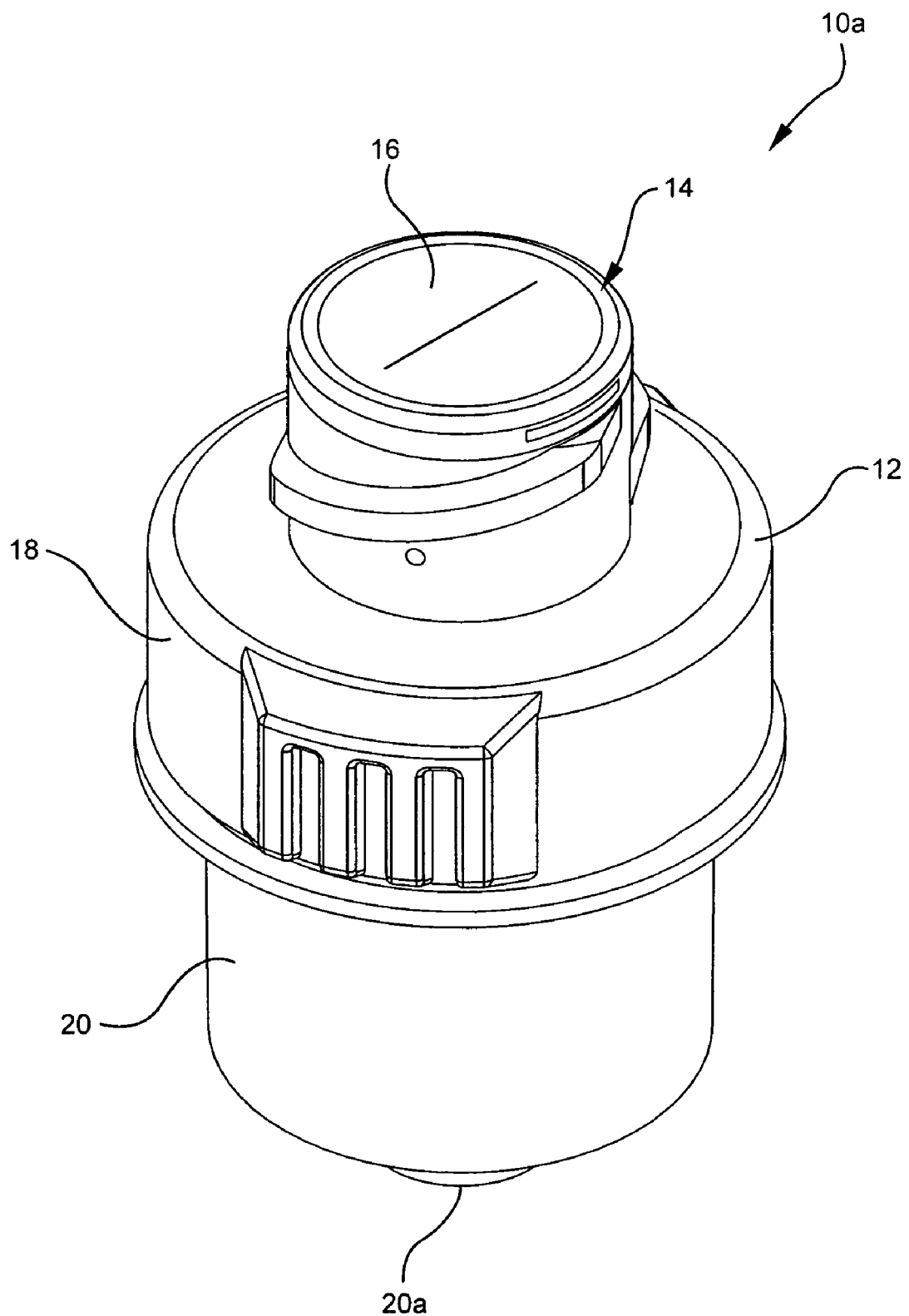
FIG. 1 is a perspective view of a first representative embodiment of an access connector.

FIG. 1 is a representative embodiment of access connector 10a. Access connector 10a includes housing 12, retaining ring 14 and septum 16. Housing 12 also includes body 18 and base 20 with patient fluid line port 20a.

Housing 12 and retaining ring 14 are typically made of thermoplastic materials such as polycarbonate, polyester and blends of the two. Retaining ring 14 may or may not be fabricated from the same polymeric material as housing 12. Septum 16 can be made from silicone or polyisoprene. A suitable material is adhesive grade liquid silicone rubber. Housing 12, retaining ring 14 and septum 16 may be fabricated from other materials as long as septum 16 is flexible, while housing 12 and retaining ring 14 are relatively rigid.

Retaining ring 14 surrounds the top of septum 16 and is attached to the top end of body 18. Base 20 is attached to the bottom end of body 18, and port 20a extends from the bottom end of base 20.

In use, connector 10a is connected to a patient fluid line via port 20a. The patient fluid line may be any of a number of types such as IV lines, saline wells, arterial lines, hemodialysis lines, etc. When connected, the system remains closed to prevent entry of microbes that could cause infection and back flow of any fluids out of the system. The Q-Syte™ closed luer access device from Becton, Dickinson and Company is an example of a connector that may be assembled according to the present invention.

Figure 2A:
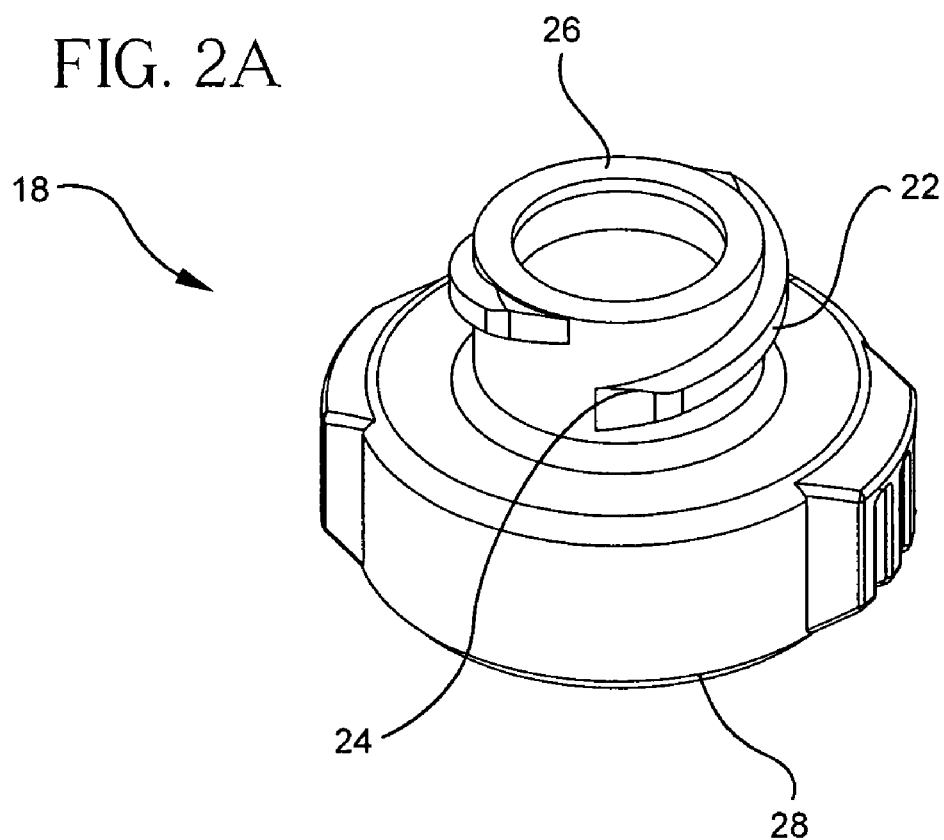
FIG. 2A is a perspective view of a body of the first access connector.
Figure 2B:
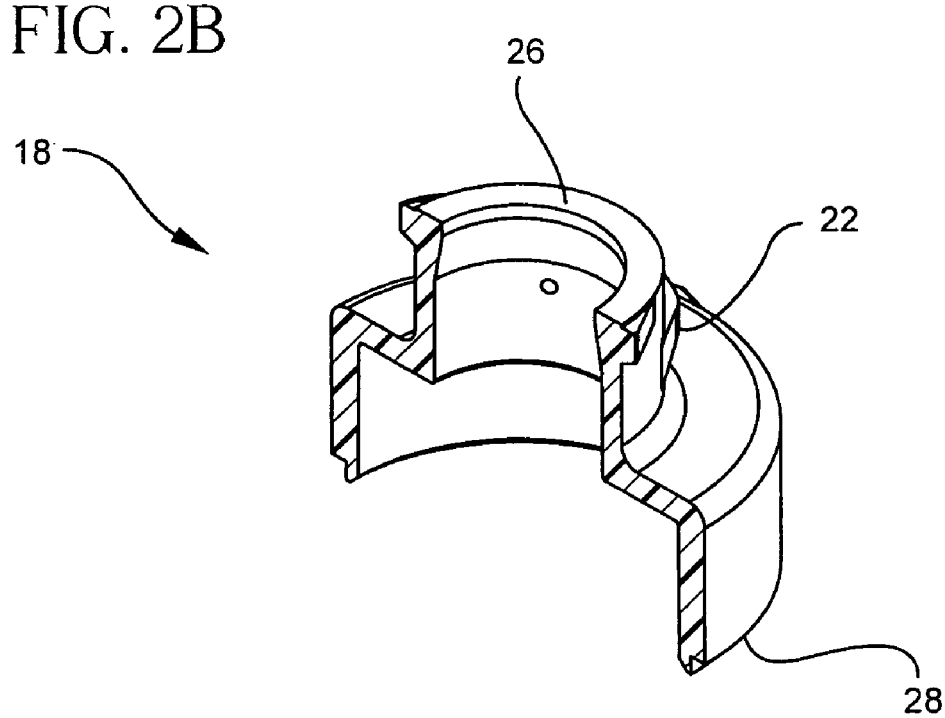
FIG. 2B is a cross-sectional view of the body of the first access connector.

FIGS. 2A and 2B show body 18 in more detail. Body 18 includes tower 22, thread 24, rim 26 and bottom edge 28. Tower 22 is the upper portion of body 18. Thread 24 extends around the external surface of tower 22, and rim 26 is at the top end of tower 22. Bottom edge 28 is at the bottom end of body 18.

Figure 3A:
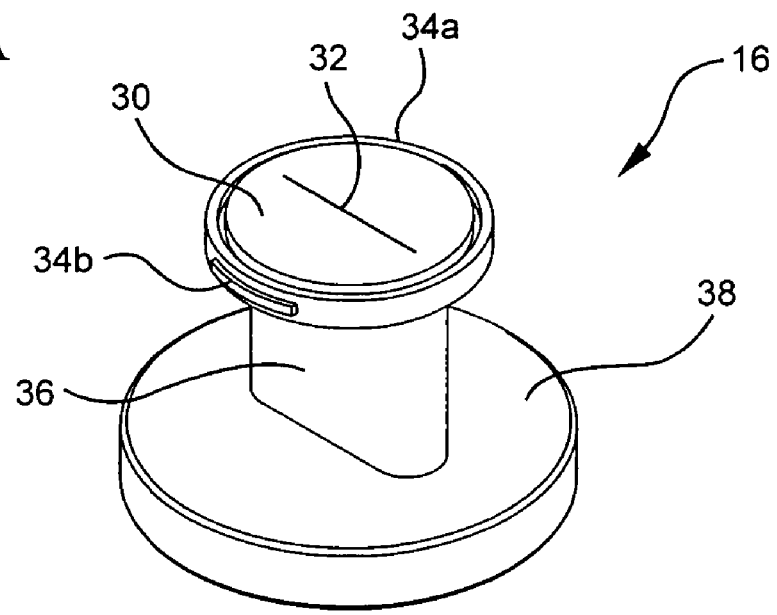
FIG. 3A is a perspective view of the septum of the first access connector.
Figure 3B:
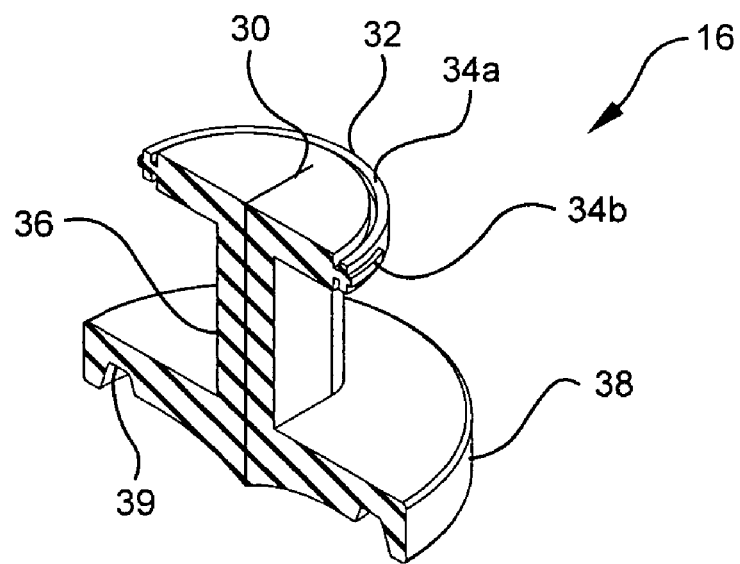
FIG. 3B is a cross-sectional view of the septum of the first access connector.

FIGS. 3A and 3B show septum 16 in more detail. Septum 16 includes top disk 30 with slit 32 and T-shaped projection 34a with flanges 34b, column 36 and bottom disk 38. FIG. 3B additionally shows annular groove 39. Top disk 30 is at the top end of septum 16. Slit 32 extends transversely near or at the middle of top disk 30, projection 34a extends around the perimeter of top disk 30 and flanges 34b are placed on opposing sides of projection 34a. Column 36 is the middle portion, and bottom disk 38 is at the bottom end of septum 16. As shown in FIG. 3B, slit 32 extends through top disk 30, column 36 and bottom disk 38, and annular groove 39 is at the underside of bottom disk 38.

Figure 4:
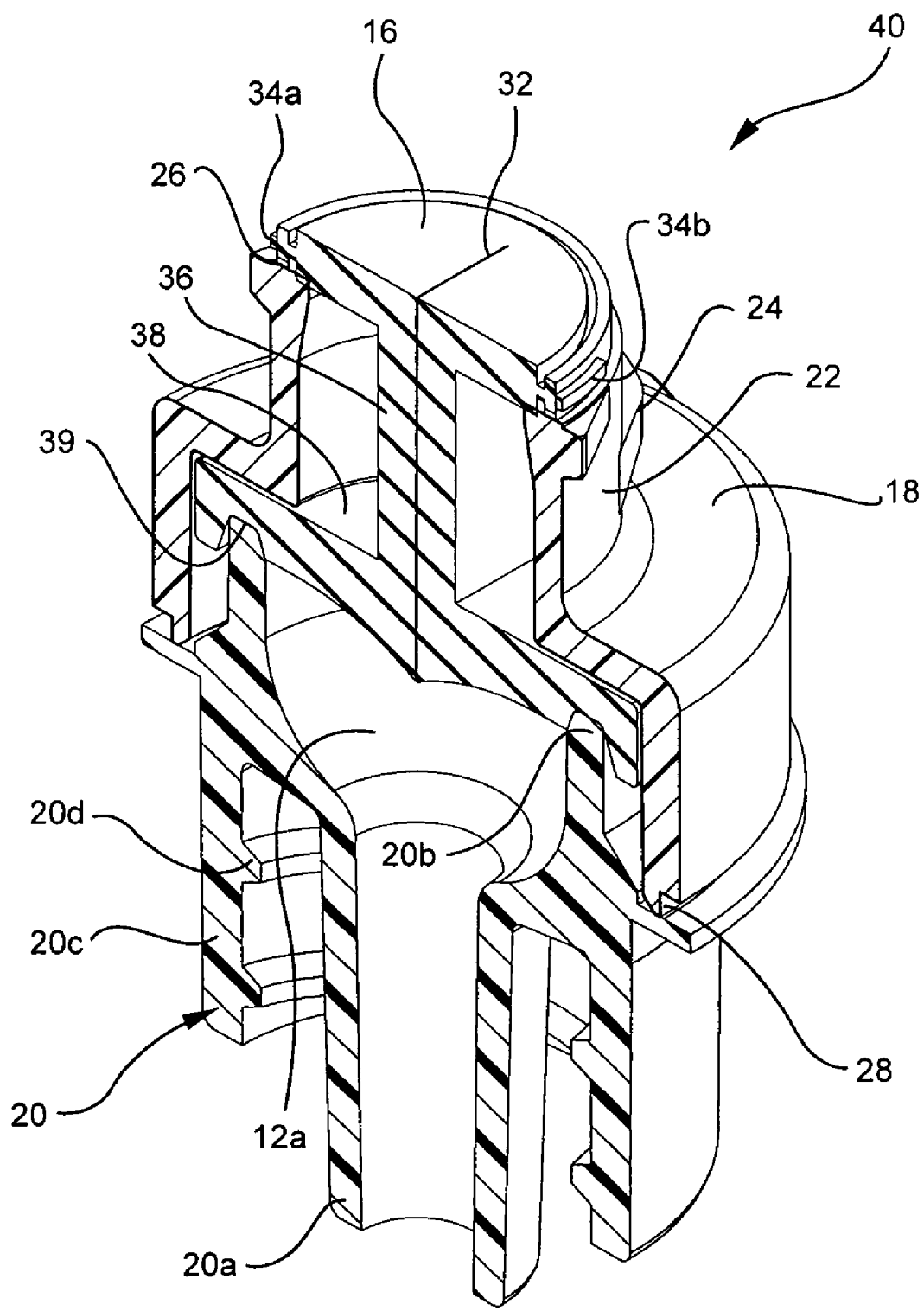
FIG. 4 is a cross-sectional view of the pre-connector of the first access connector.

FIG. 4 shows a representative embodiment of pre-connector 40, which includes septum 16, body 18 and base 20. Fluid channel 12a is defined by septum 16, body 18 and base 20. Base 20 includes port 20a, rim 20b, sleeve 20c and thread 20d. In other embodiments, base 20 is not included in pre-connector 40 and is added later in the manufacturing process.

Body 18 and base 20 are formed separately, typically by injection molding. In that process, the thermoplastic material used for body 18 and base 20 is rigid at room temperature and melted just prior to injecting under pressure into body-shaped and base-shaped molds. The thermoplastic material cools and solidifies taking the shape of the mold cavity. Once cooled, body 18 and base 20 are de-molded.

Septum 16 is also typically formed by injection molding. A two-component silicone is injected into a heated septum-shaped mold cavity under pressure. The two components, which are liquid at room temperature, contact the hot mold, and react and solidify taking the shape of the mold cavity. Septum 16 is de-molded while still hot and allowed to cool outside of the mold.

To assemble pre-connector 40, bottom disk 38 of septum 16 is collapsed and inserted through tower 22 and opens within body 18. Alternatively, top disk 30 is collapsed and inserted through tower 22 and opens above rim 26 of body 18. Base 20 is then positioned such that it engages bottom edge 28 of body 18 and rim 20b mates with annular groove 39 of septum 16 to seal and define fluid channel 12a. Also, septum 16 is pushed up the necessary amount to create space for the injection between T-shaped projection 34a and rim 26 of body 18. At this point, body 18 and base 20 may be bonded by processes such as ultrasonic welding, solvent bonding, adhesive bonding, etc. These sections readily bond, as they are fabricated from the same or same class of materials. However, base 20 may be attached at a later point in the manufacturing process.

As noted above, projection 34a sits slightly above rim 26 of tower 22. To finish assembly of connector 10a, retaining ring 14 is overmolded by injection molding onto pre-connector 40. The injection molding process is typically carried out by insert molding and involves two dissimilar materials, thermoplastic and silicone, being brought together into one molding operation. Pre-connector 40 is placed within such that top disk 30 of septum 16 partially defines a retaining ring-shaped mold. Molten thermoplastic material, which is a material that will bond to body 18, is injected into the mold cavity and allowed to cool. Once cooled, connector 10a (as shown in FIG. 1) is de-molded.

Figure 5:
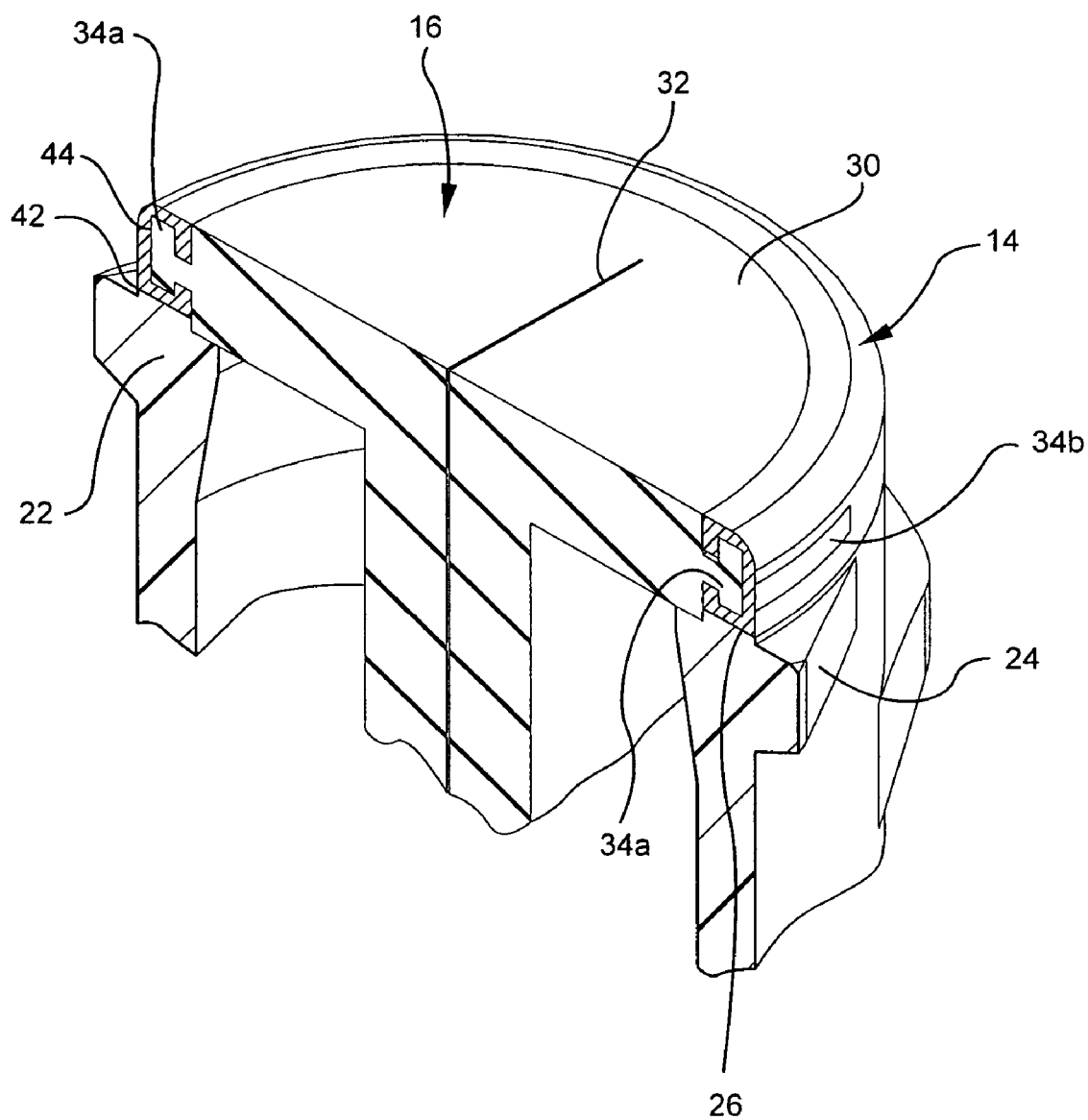
FIG. 5 is a cross-sectional view of the top portion of the first access connector.

FIG. 5 shows the top portion of connector 10a in more detail. FIG. 5 includes retaining ring 14, septum 16 and tower 22. Interface 42 between retaining ring 14 and rim 26 of tower 22 and interface 44 between retaining ring 14 and septum 16 are also indicated.

Because retaining ring 14 sits slightly above rim 26, it encompasses T-shaped projection 34a to create a mechanical attachment between the two parts. Geometry other than T-shaped geometry may also be used to create a projection for mechanical attachment as long as axial movement between septum 16 and housing 12 is minimized, which is important for preventing septum 16 from slipping out of housing 12 or snapback during use. In addition, flanges 34b, which may also take on other configurations, minimize rotational movement between septum 16 and housing 12. As will become apparent, septum 16 is positioned within retaining ring 14 such that the ingress of microbes through septum 16 is minimized and rotational movement between septum 16 and housing 12 may slightly reduce the ability of connector 10a prevent microbial ingress.

Retaining ring 14 and tower 22 are attached at interface 42 typically by one of two methods. The first method involves chemical adhesion during the injection molding process. In this embodiment, rim 26 slightly melts at interface 42 when the molten thermoplastic is injected for formation of retaining ring 14 resulting in fusion between the parts.

In the second method, retaining ring 14 and rim 26 are mechanically bonded or chemically bonded by processes such as ultrasonic welding, solvent bonding, adhesive bonding, etc. These sections readily bond, because they are fabricated from the same or same class of materials. It is important to note that any combination of attachment or bonding may be used at interfaces 42 and 44.

Once assembled, connector 10a is used to access a patient fluid line. A medical device having a tubular portion, such as a male luer taper of a syringe, is used to infuse or withdraw fluids from the patient fluid line via connector 10a. The male luer taper is inserted into slit 32 of septum 16 and, if the medical device has a luer lock, rotated to interlock the medical device with connector 10a via thread 24. Medical devices that utilize a luer slip can also be used with connector 10a by simply sliding the male luer taper in place. Connector 10a may be fabricated without thread 24, but then connector 10a could only be used in combination with a luer slip and not a luer lock.

When the male luer taper is in place, a clinician is then able to either infuse the patient fluid line or draw fluids from it. Medical devices having a luer lock are rotated in the opposite direction and pulled out for withdrawal from septum 16, while medical devices having a luer slip are simply pulled out. The system remains closed, and the risk of entry by microbes or leakage of contaminated fluids is minimized. In addition, there is no threat of accidental needle sticks.

The male luer taper must be inserted into, withdrawn from and rotated within septum 16, and connector 10a must be able to perform optimally after multiple uses. Attaching septum 16 to retaining ring 14 minimizes axial and rotational movement of septum 16 relative to housing 12 to maintain optimal performance. For instance, consistent attachment between septum 16 and retaining ring 14 minimizes snapback, which was previously described.

As is evident from the Figures, the components of housing 12 and septum 16 create channel 12a through connector 10a. Septum 16 acts as resealable seal that allows fluid to pass through when septum 16 is opened by a tubular portion of a medical device.

Retaining ring 14 is typically shaped to exert a compressive force on septum 16 to bias slit 32 closed. Retaining ring 14 may be molded to take on an elliptical shape and positioned relative to slit 32 such that the longitudinal axis of slit 32 is aligned with the longitudinal, uncompressed axis of retaining ring 14.

Alternatively, if retaining ring 14 is attached to tower 22 after the injection molding process, retaining ring 14 may be deformed to take on the elliptical shape. Deforming ring 14 is relatively easy, because its small size makes it quite malleable. A slight force applied on each side of retaining ring 14 is enough to deform it into the elliptical shape, and it may be deformed prior to or as it is being attached to tower 22. Tower 22, which is much more rigid than retaining ring 14, maintains retaining ring 14 in the elliptical configuration.

The present invention improves the manufacture of connector 10a by eliminating the use of primer and adhesive to bond housing 12 and septum 16.

Thus, restrictions on scaling up to high volume production are reduced. In addition, interface 42 is stronger and more consistent than the adhesive bonds. Variations in the configuration of the top disk and retaining ring may provide additional advantages. Examples are described below.

Figure 6:
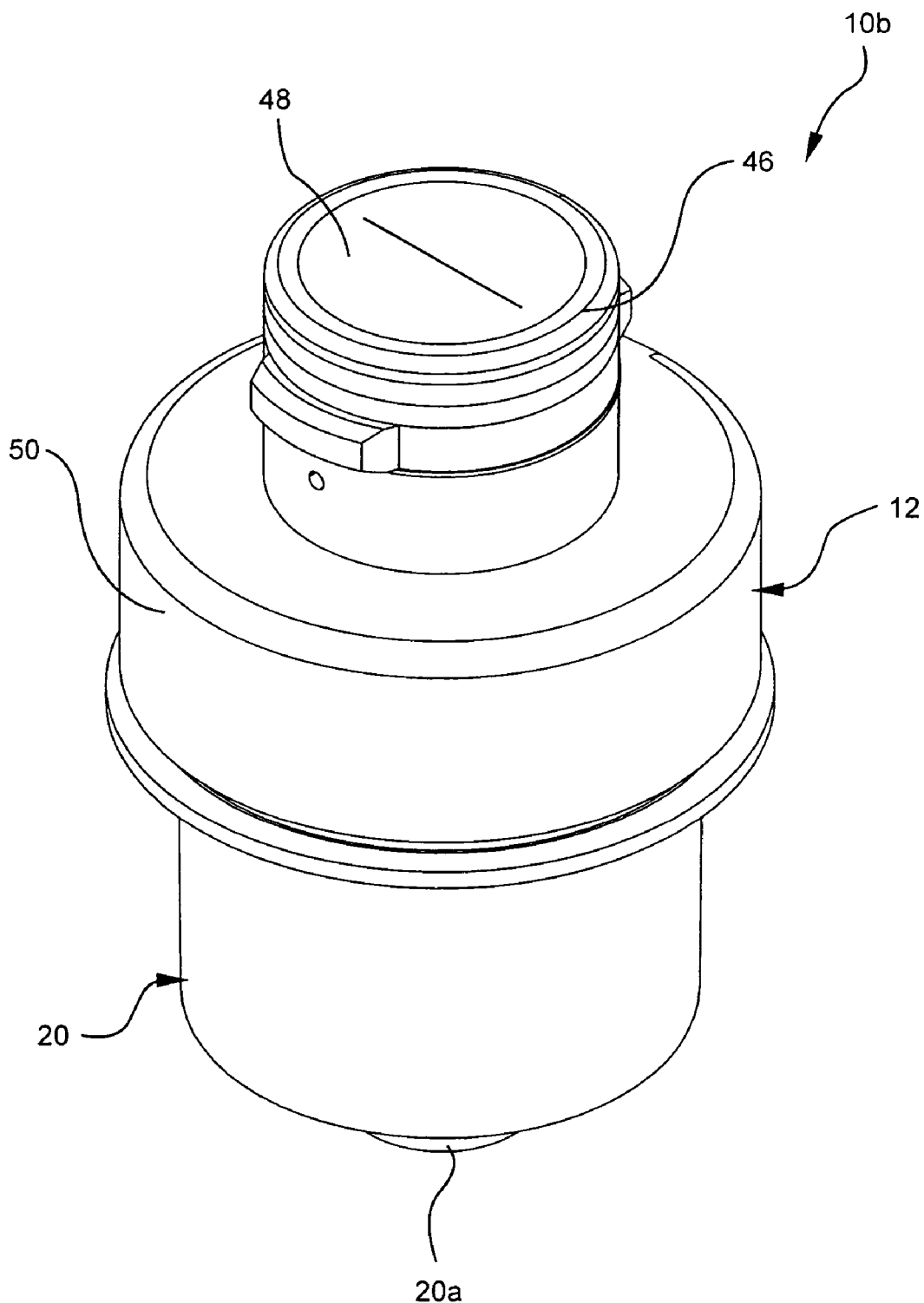
FIG. 6 is a perspective view of a second representative embodiment of an access connector.

FIG. 6 is a representative embodiment of access connector 10b. Connector 10b includes housing 12 having body 50 and base 20, retaining ring 46 and septum 48. Base 20 includes patient fluid line port 20a.

Figure 7A:
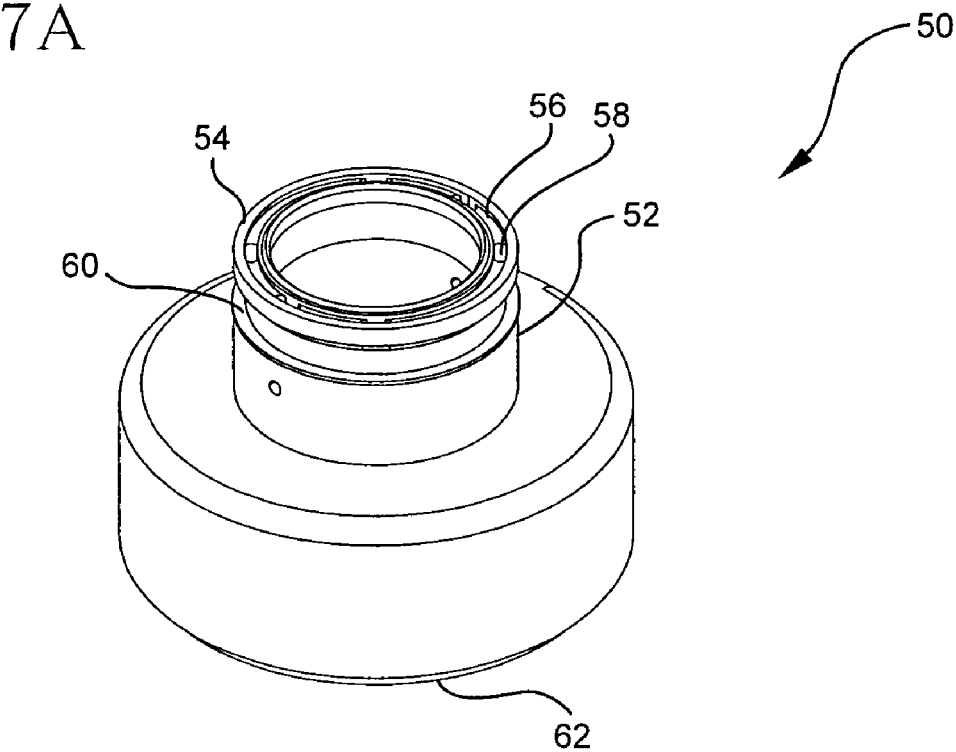
FIG. 7A is a perspective view of a body of the second access connector.
Figure 7B:
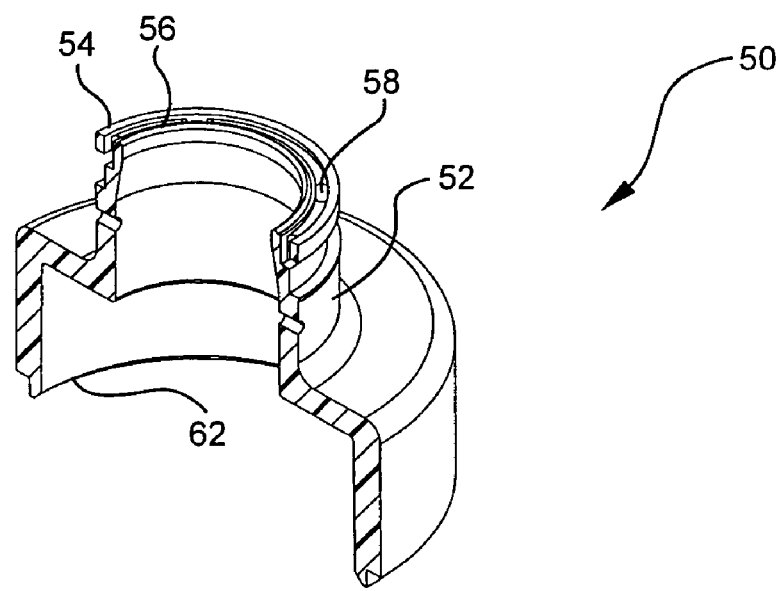
FIG. 7B is a cross-sectional view of the body of the second access connector.

FIGS. 7A and 7B show body 50 in more detail. Body 50 includes tower 52 and bottom edge 62. Tower 52 also includes projection 54, slot 56, pores 58 and channel 60. Projection 54, slot 56, pores 58 and channel 60 create geometry for mechanical coupling to retaining ring 46. Examples of geometry include pores, undercuts and increased surface area.

Figure 8A:
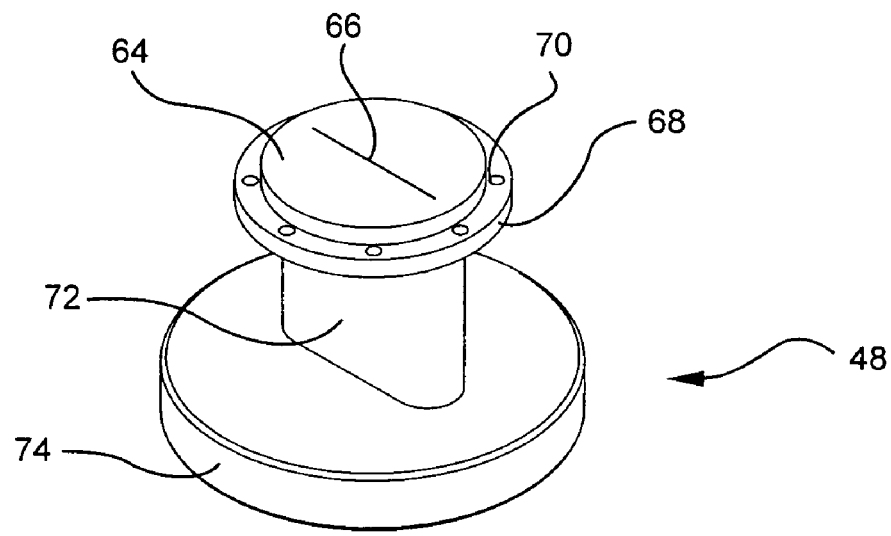
FIG. 8A is a perspective view of the septum of the second access connector.
Figure 8B:
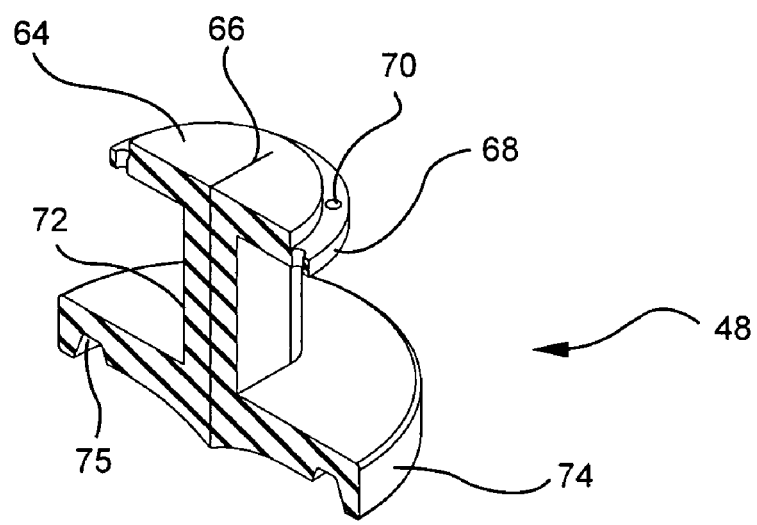
FIG. 8B is a cross-sectional view of the septum of the second access connector.

FIGS. 8A and 8B show septum 48 in more detail. Septum 48 includes top disk 64 with slit 66, flange 68 and pores 70, column 72 and bottom disk 74 with annular groove 75. Flange 68 and pores 70 also create geometry for mechanical coupling to retaining ring 46.

Figure 9:
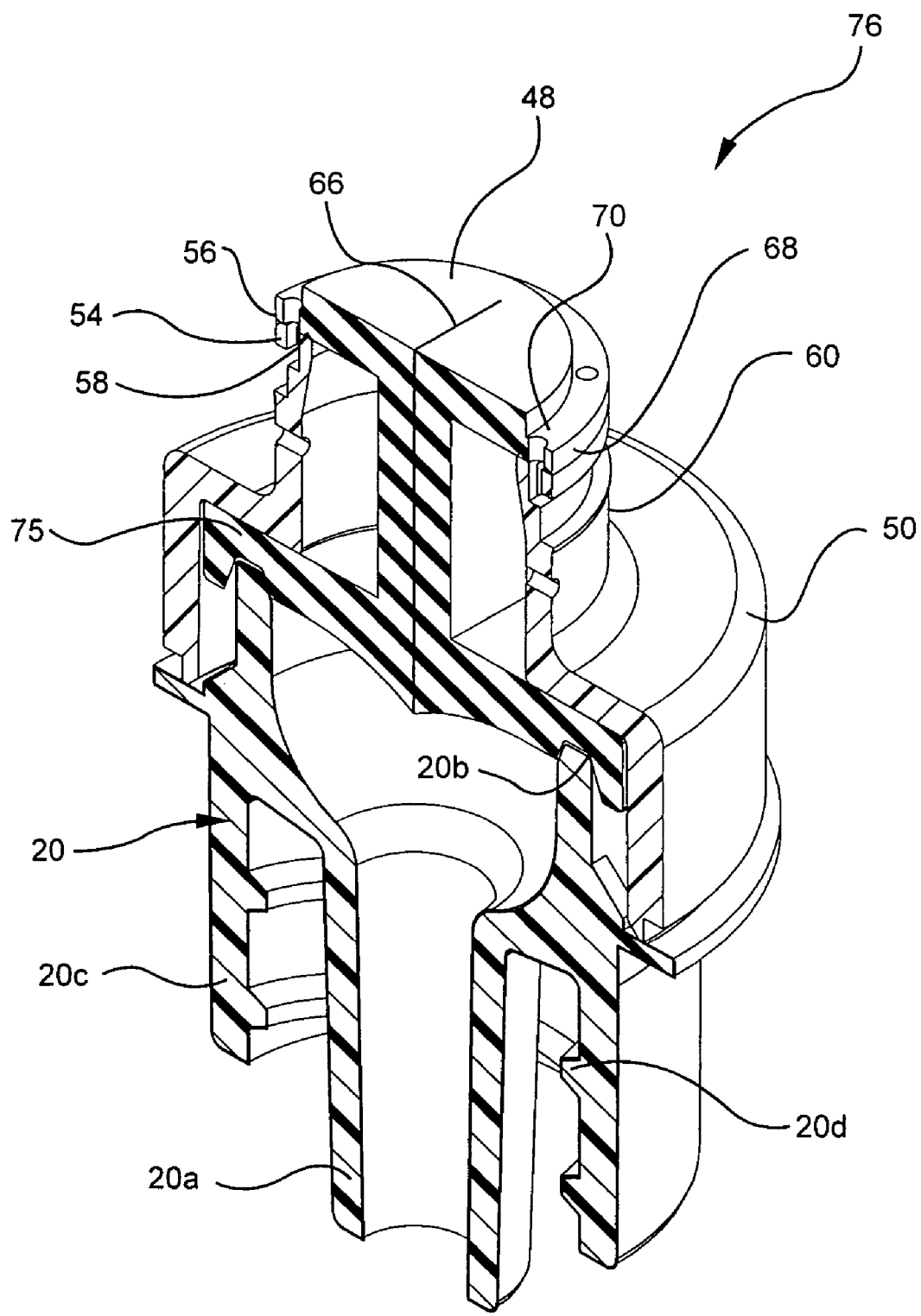
FIG. 9 is a cross-sectional view of the pre-connector of the second access connector.

Septum 48, body 50 and base 20 are assembled as described above to form pre-connector 76, which is shown in FIG. 9. In this embodiment, flange 68 of septum 48 rests on projection 54 of body 50. Pores 70 and 58 are shown aligned, but this is not critical. Retaining ring 46 is then overmolded onto preconnector 76 to finish connector 10b by inserting pre-connector 76 into a retaining ring-shaped mold cavity that is partially defined by pre-connector 76.

Figure 10:
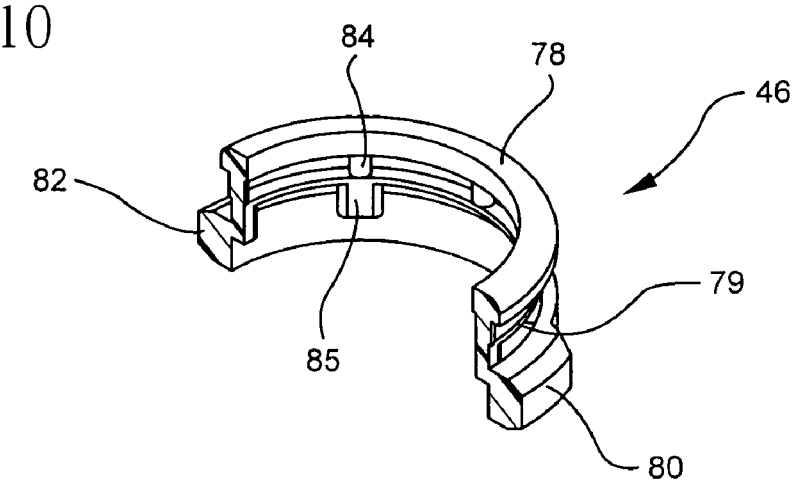
FIG. 10 is a perspective view of a retaining ring of the second access connector.

Though retaining ring 46 is not formed without pre-connector 76, FIG. 10 shows only retaining ring 46 for clarity. Retaining ring 46 includes top ring 78, middle ring 79, bottom ring 80 with lugs 82 and connecting bars 84 and 85. Lugs 82 create a luer lock on connector 10b. Bars 84 connect top ring 78 and middle ring 79, and bars 85 connect middle ring 79 and bottom ring 80. Rings 78, 79 and 80 and bars 84 and 85 provide extensive geometry for mechanical coupling with septum 48 and body 50.

Figure 11:
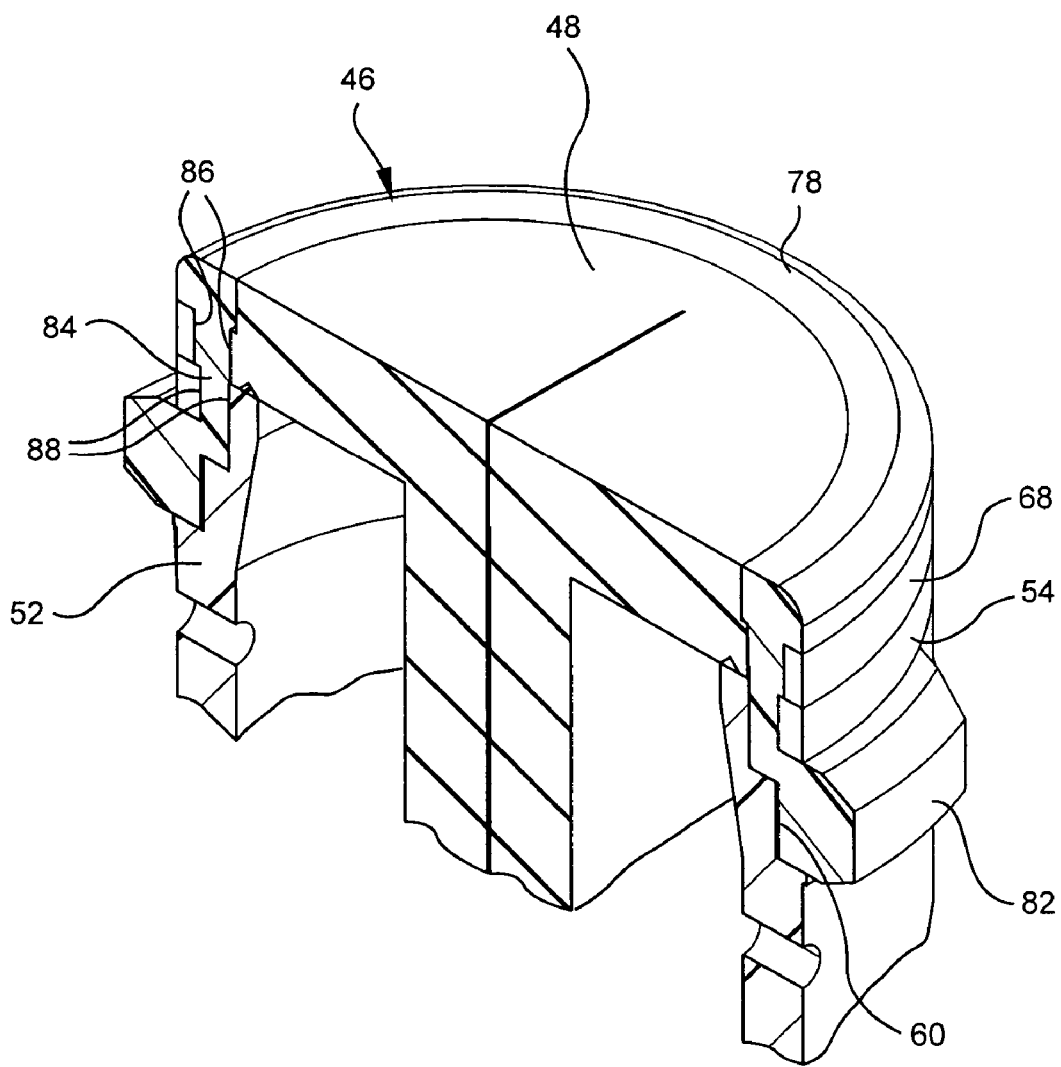
FIG. 11 is a cross-sectional view of the top portion of the second access connector.

FIG. 11 shows the top portion of connector 10b in more detail and additionally shows interface 86 between retaining ring 46 and septum 48 and interface 88 between retaining ring 46 and tower 52. Top ring 78 of ring 46 sits on ridge 68 of septum 48. Bars 84 extend from top ring 78 through pores 70 to middle ring 79. Bars 85 extend from middle ring 79 through pores 58 to bottom ring 80. Middle ring 79 is positioned within slot 56, and bottom ring 80 sits within channel 60 of tower 52. As is evident from the Figures, much of the structure of retaining ring 46 is defined by the geometry of septum 48 and body 50.

This configuration provides mechanical coupling between retaining ring 46, septum 48 and body 50 that minimizes both axial and rotational movement between septum 48 and housing 12. Thus, interfaces 86 and 88 may or may not be attached via chemical adhesion. Where attachment is based solely on mechanical means, the molten material forming retaining ring 46 solidifies around septum 46 and body 50 without fusing to their surfaces.

Figure 12:
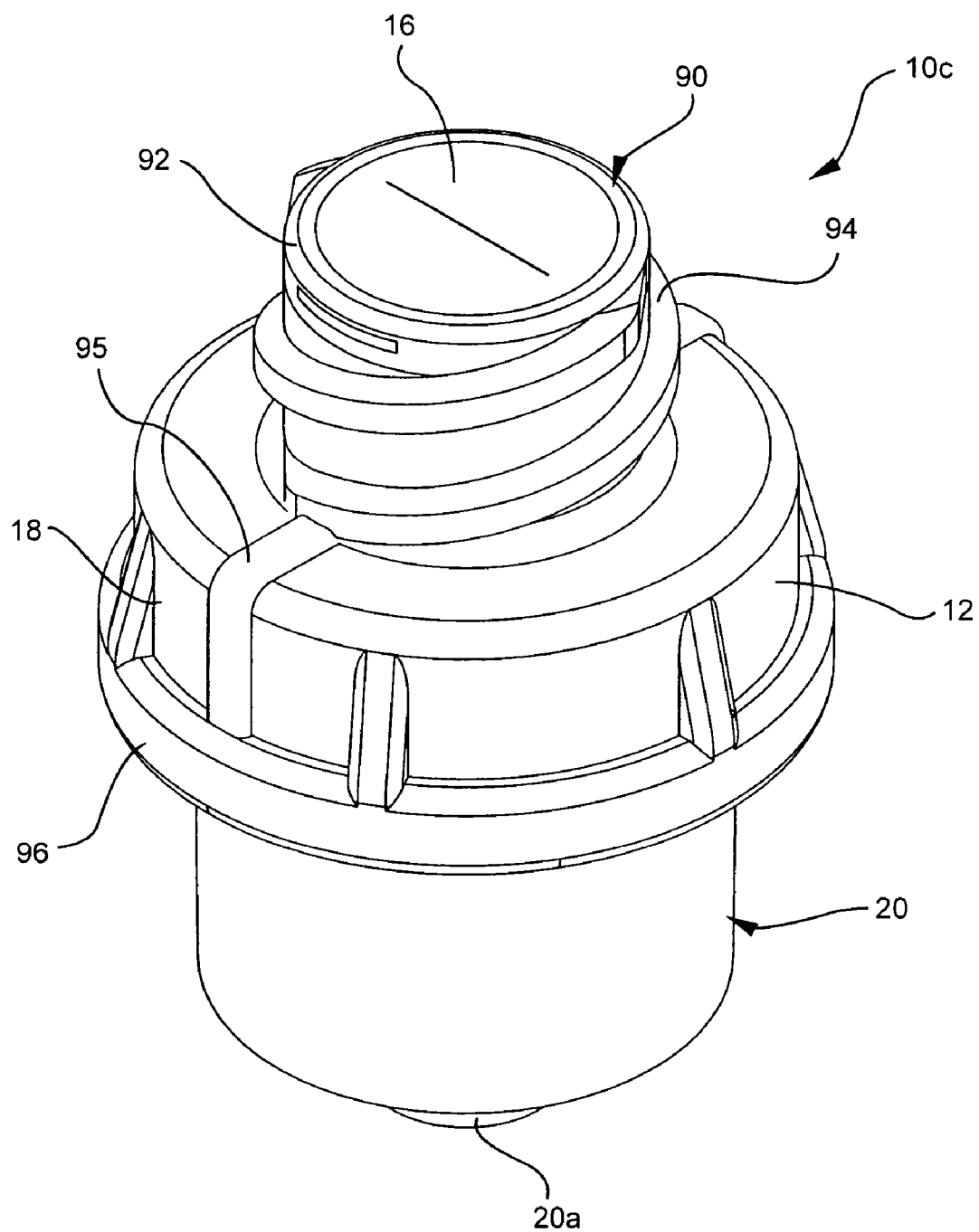
FIG. 12 is a perspective view of a third representative embodiment of an access connector.

FIG. 12 is a representative embodiment of access connector 10c. Connector 10c includes housing 12 with body 18 and base 20, septum 16 and retaining ring 90. Retaining ring 90 also includes ring 92, thread 94, arms 95 and cage 96. In this example, the configuration of ring 92 and septum 16 is identical to that of connector 10a (refer to FIG. 5). However, retaining ring 90 additionally provides thread 94 and cage 96.

Figure 13:
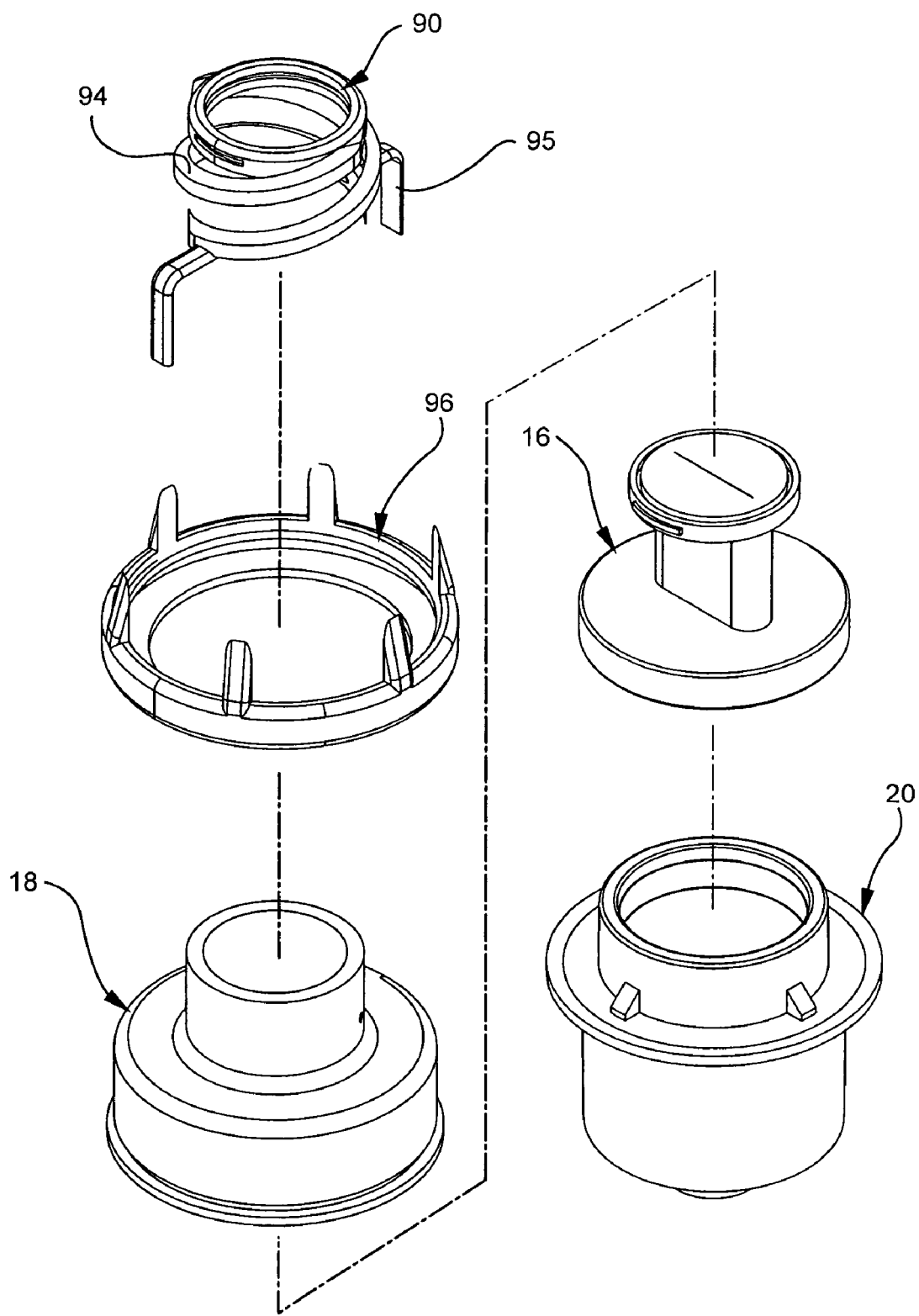
FIG. 13 is an exploded view of the third access connector.

FIG. 13 shows individual parts of connector 10c. It should be noted that any of the parts that make up retaining ring 90 may be connected to each other or be separate from each other and still be within the scope of the present invention. For example, it is not essential that arms 95 be connected to thread 94.

Thread 94 serves two purposes. First, it is the means for a luer lock for securing to a syringe or other medical device. Second, it increases the surface area of the interface between retaining ring 90 and body 18. The increased surface area provides more area for attachment, through chemical adhesion and/or mechanical attachment, for stronger bonds between the parts.

Cage 96 also serves dual purposes. First, it creates grips along connector 10c for the clinician to grasp during use. Second, it attaches body 18 to base 20 by mechanical attachment and/or chemical adhesion.

Arms 95 are typically attached to cage 96 and are the result of a fluid channel between thread 94 and cage 96. The fluid channel allows retaining ring 90 to be formed in one step. Arms 95 also act as a gripping surface.

Figure 14:
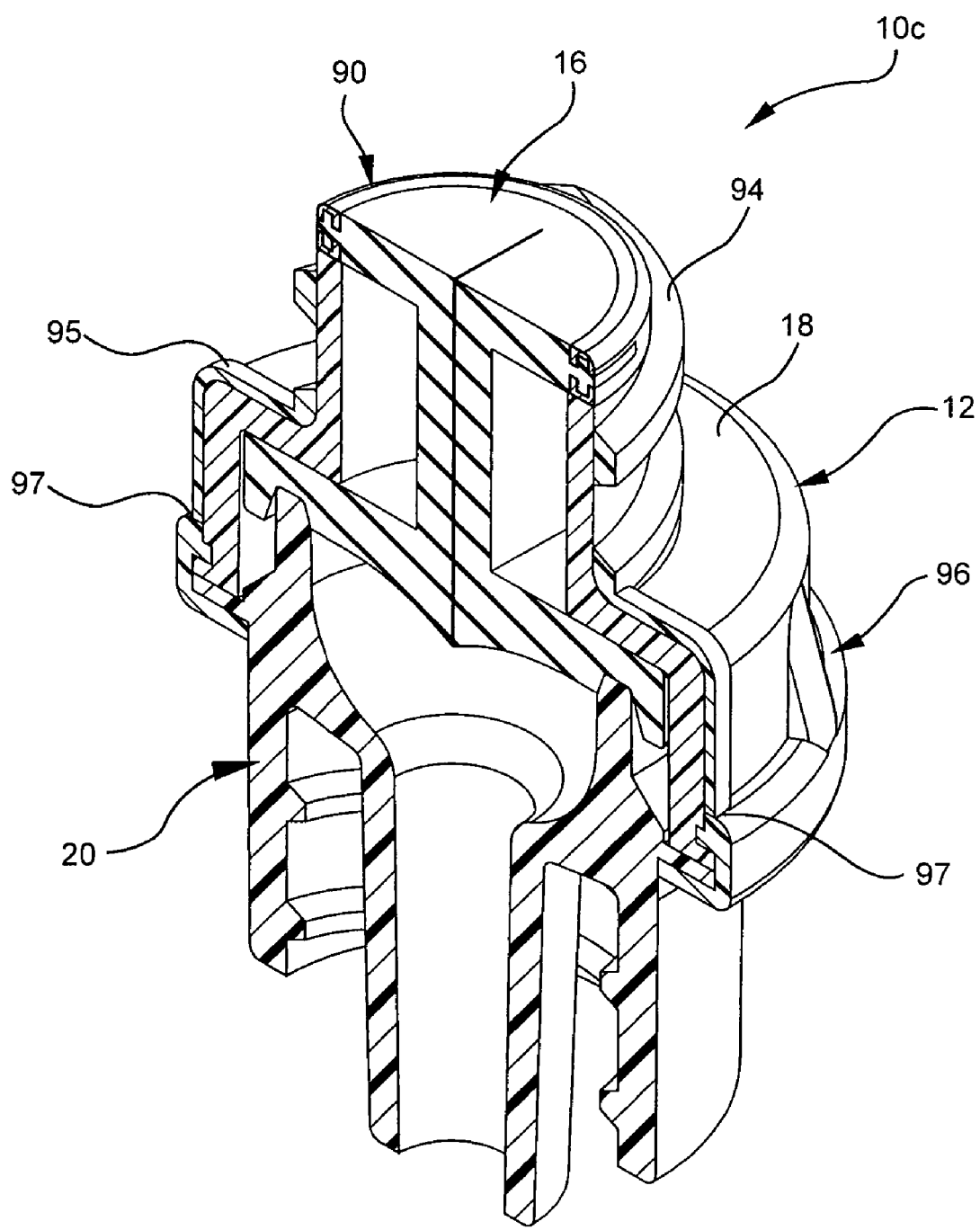
FIG. 14 is a cross-sectional view of the third access connector.

FIG. 14 shows attachment of body 18 and base 20 by arms 95 and cage 96 in more detail. Bonding at interface 97 between arms 95 and cage 96 prevents connector 10c from being disassembled. In this embodiment, the formation of a bond as an individual step between body 18 and base 20 is not necessary, and attachment of every component of connector 10c can be carried out in one injection molding step. Alternatively, ring 92, thread 94 and arms 95 with septum 16 may be fabricated as a first piece, and cage 96 fabricated as a second piece. The first and second pieces can then be assembled with body 18 and base 20, and arms 95 and cage 96 are subsequently bonded by any of the means previously described to form connector 10c.

The configurations of the retaining rings presented above are only examples. Other geometries may also be used that will impart the advantages of the invention.

Figure 15:
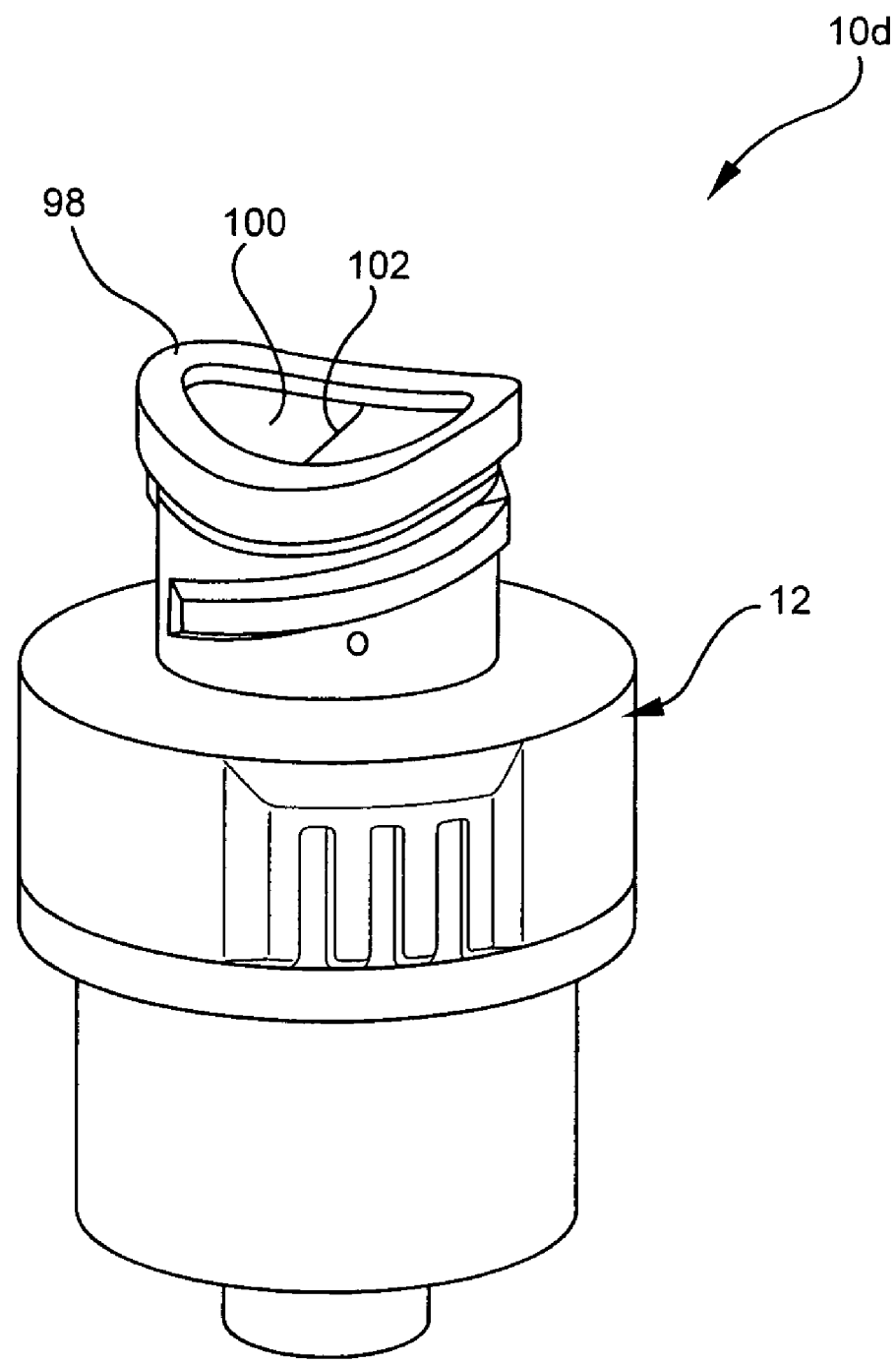
FIG. 15 is a perspective view of a fourth representative embodiment of an access connector.

Another variation is shown in FIG. 15, which is a representative embodiment of connector 10d. Connector 10d includes housing 12, retaining ring 98 and septum 100 with slit 102. Here, retaining ring 98 and septum 100 are similar to retaining ring 14 and septum 16 of connector 10a except that retaining ring 98 and septum 100 have a saddle configuration at the top of connector 10d. The saddle configuration provides additional bias to compress slit 102 and may be combined with any configuration of connector 10 to give the advantage of biasing slit 102 closed in order to maintain a closed system.

Figure 16A:
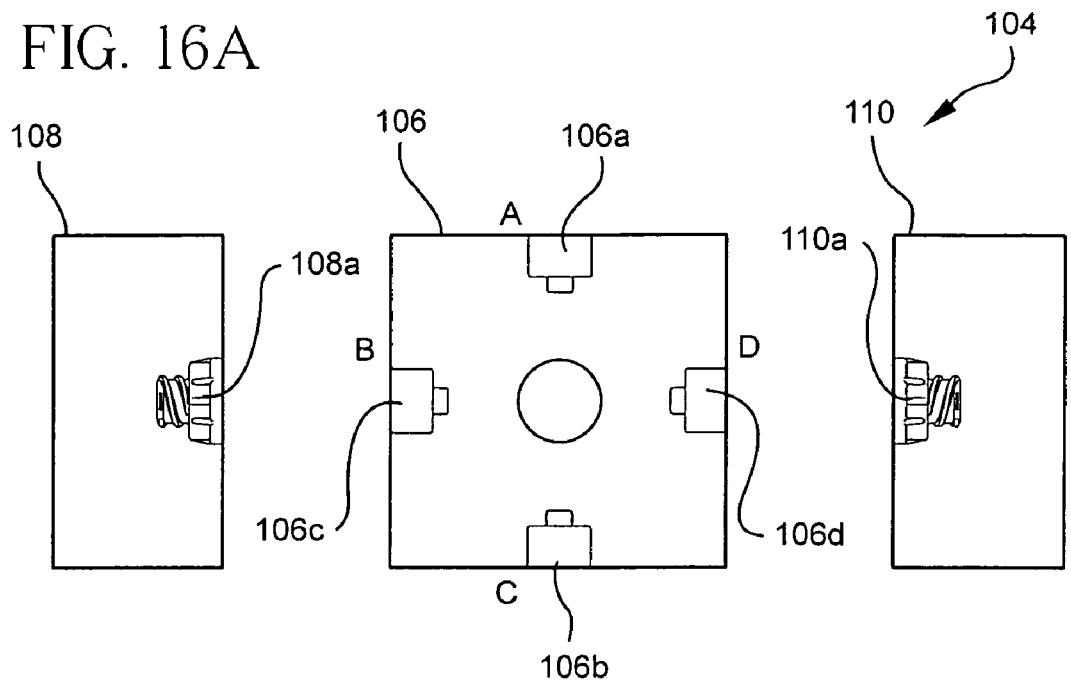
FIGS. 16A-16F are cross-sectional views of a representative method of making an access connector.

FIGS. 16A-16F illustrate a representative embodiment for making an access connector with this particular example showing the manufacture of connector 10c (FIG. 12). FIG. 16A shows mold system 104 with carrier 106 and molds 108 and 110. Carrier 106 includes receptacles 106a, 106b, 106c and 106d. FIG. 16A also shows positions A, B, C and D. Receptacle 106a is at position A, receptacle 106b is at position C, receptacle 106c is at position B and receptacle 106d is at position D. Mold 108 includes mold cavity 108a, and mold 110 includes mold cavity 110a.

Figure 16B:
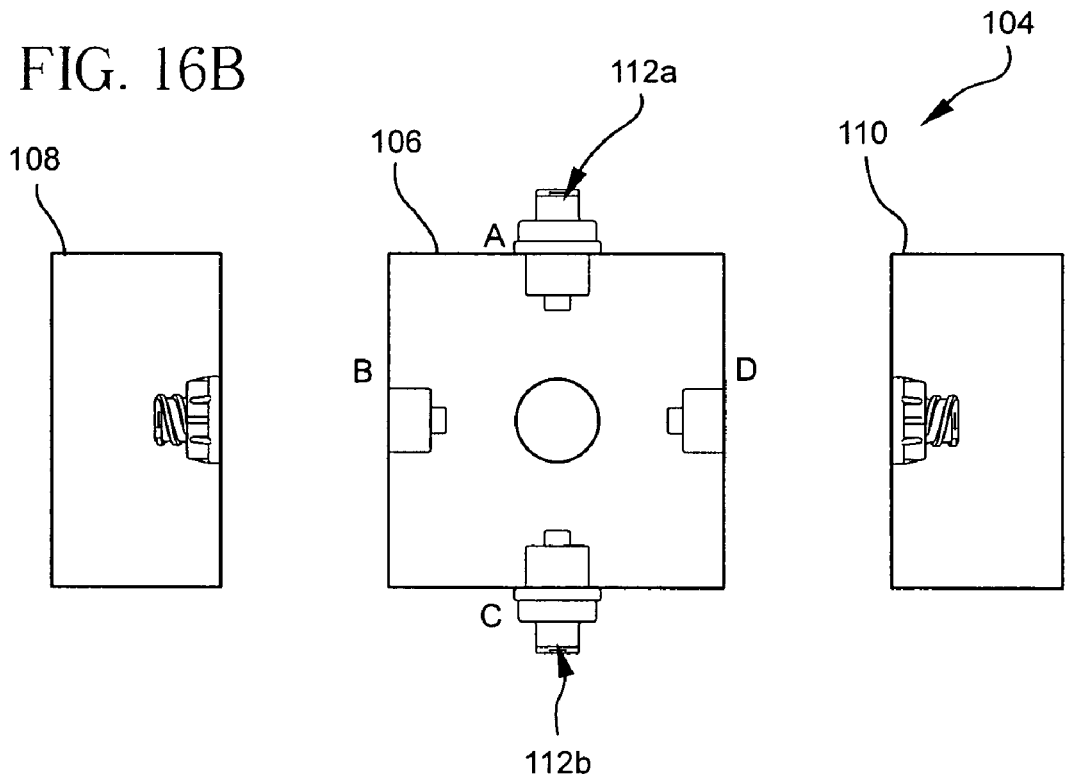
Figure 16C:
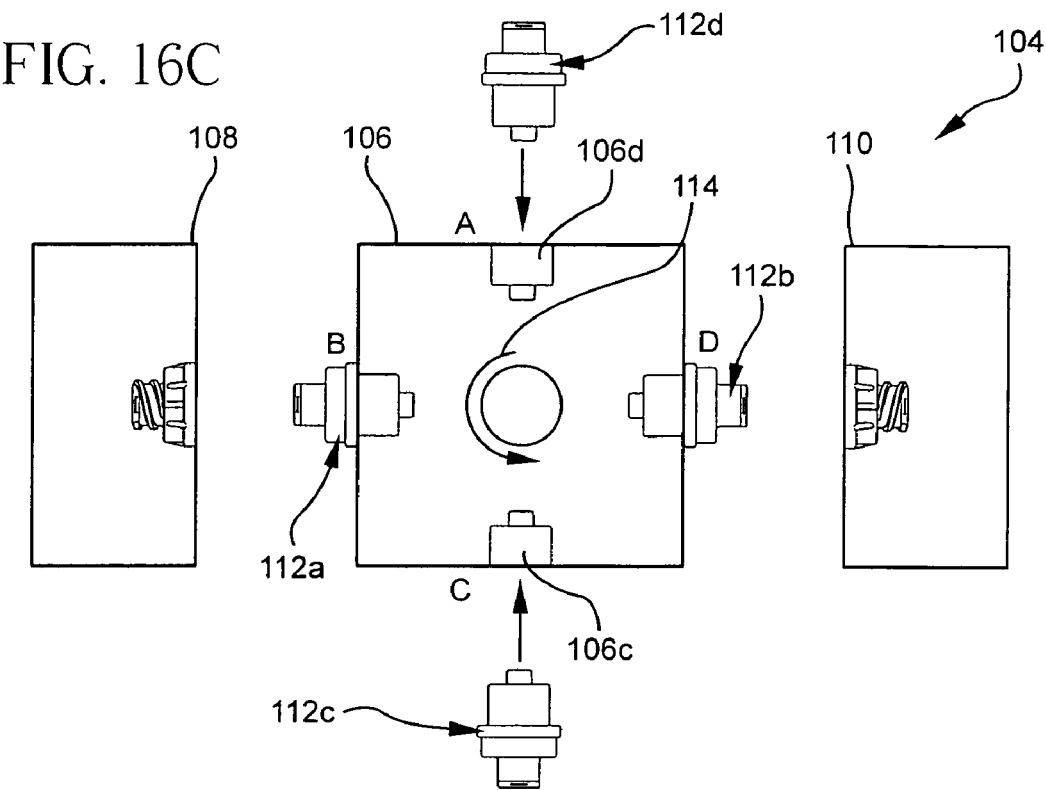

FIG. 16B shows insertion of pre-connectors 112a and 112b into receptacles 106a and 106b, respectively. Carrier 106 is then rotated about 90° in a direction indicated by arrow 114 shown in FIG. 16C. Upon rotation, pre-connectors 112a and 112b are now at positions B and D, respectively, and pre-connectors 112c and 112d are inserted into receptacles 106c and 106d, respectively.

Figure 16D:
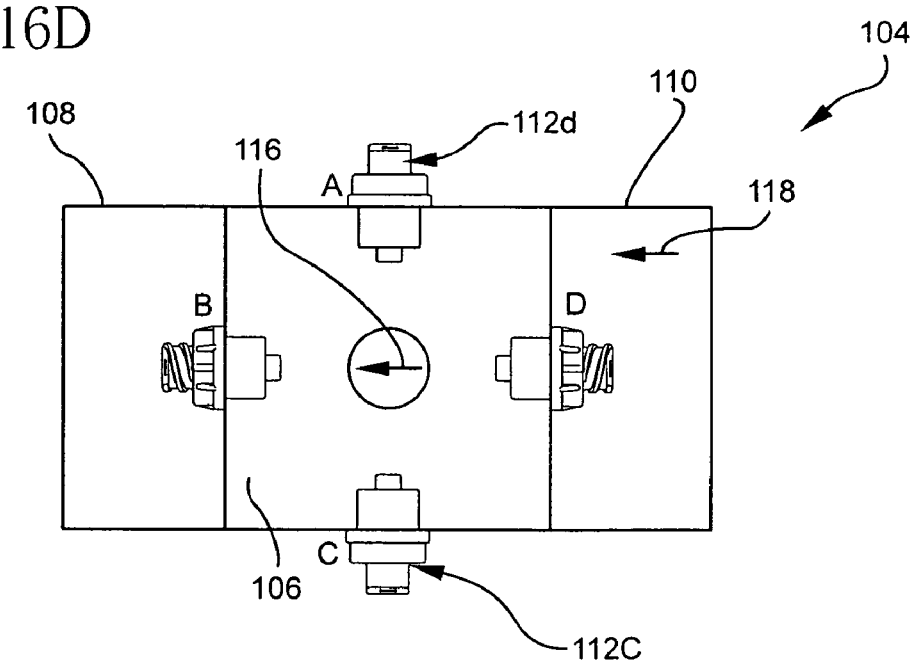

As shown in FIG. 16D, carrier 106 and mold 110 are moved transversely in a direction indicated by arrows 116 and 118, respectively, until carrier 106 is coupled with mold 108, and mold 110 is coupled with carrier 106. Pre-connectors 112a and 112b are within mold cavities 108a and 110a, respectively, which are shaped for the addition of retaining ring 90.

At this point, the injection molding process takes place to form retaining ring 90 around pre-connectors 112a and 112b.

Figure 16E:
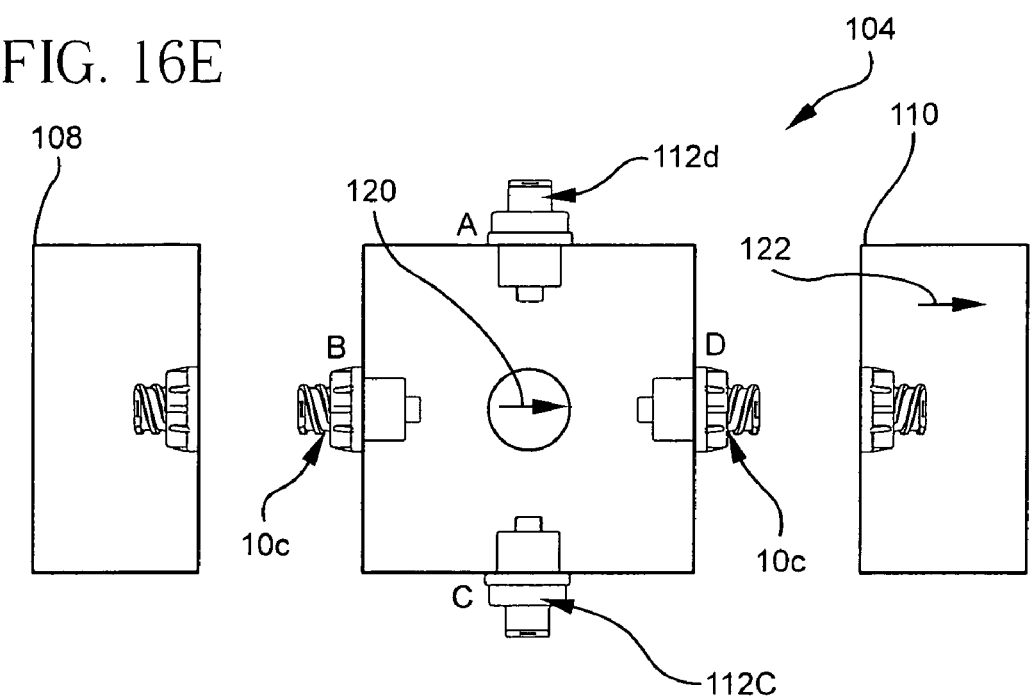

Once molds 108 and 110 cool, carrier 106 and mold 110 move transversely in a direction indicated by arrows 120 and 122, respectively, back to their original positions. This step is illustrated in FIG. 16E. The process results in connectors 10c at positions B and D.

Figure 16F:
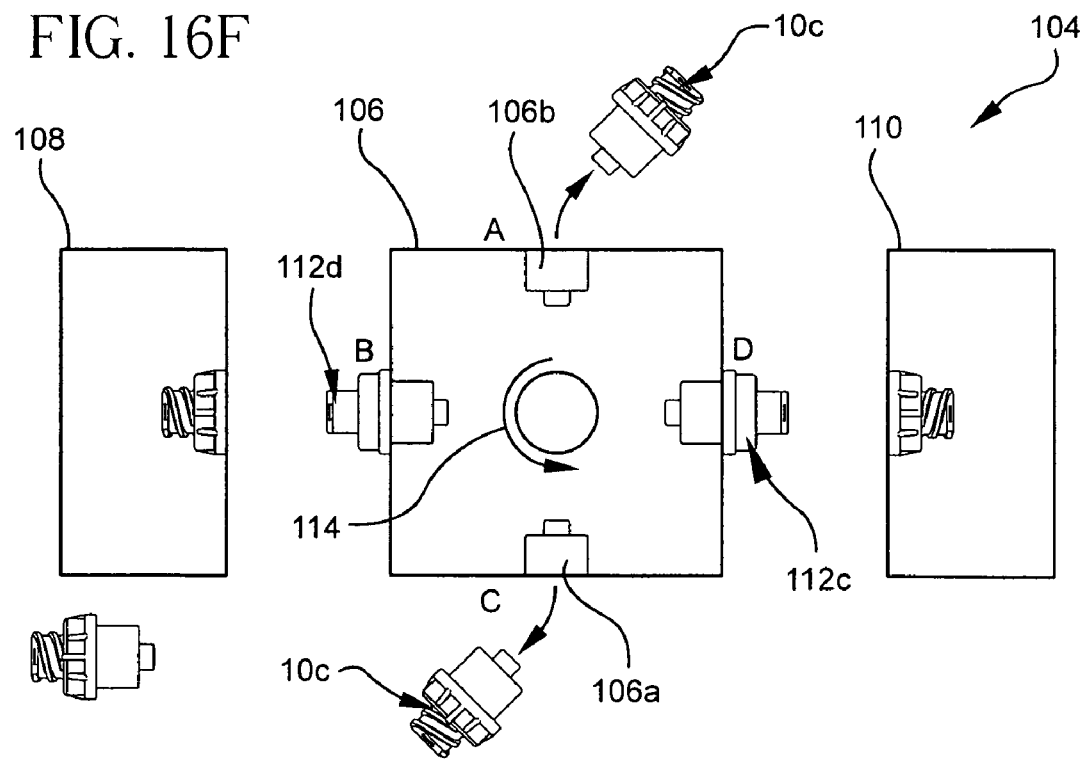

Carrier 106 is again rotated 90° in the direction indicated by arrow 114 as shown in FIG. 16F. Connectors 10c are ejected from receptacles 106a and 106b. Pre-connectors 112c and 112d, located at positions D and B, respectively, are now in position for accepting molds 108 and 110 to continue the process.

Molding a retaining ring around the septum of access connectors according to the present invention provides several advantages. The attachment between the parts is strong and consistent. In addition, the process is a method that can be scaled up for high volume production.

Although the present invention has been described with reference to preferred embodiments, workers skilled in the art will recognize that changes may be made in form and detail without departing from the spirit and scope of the invention.

The invention claimed is:

1. An access connector comprising:
   a housing having a body, a base, and a channel for fluid passage extending through the body and the base, the body including a tower with a top rim and a bottom end attached to the base;
   a septum having a top disk, a bottom disk, a column, and a slit extending from the top disk through the column to the bottom disk, the septum positioned within the channel to allow for insertion of a tubular portion of a medical device, the bottom disk of the septum being positioned in the bottom end of the body, the column extending through the tower without contacting the tower, and the top disk being positioned above the top rim of the body; and
   a retaining ring of a different material than the septum overmolded around and integrally joined to the top disk of the septum so that mating features on the retaining ring and septum mate and form an integral unit to prevent axial displacement and rotational movement of the septum, the retaining ring having a bottom end attached to the top rim of the tower thereby securing the septum with respect to the housing.

2. The access connector of claim 1 wherein the septum and retaining ring are attached by chemical adhesion, mechanical attachment or a combination thereof.

3. The access connector of claim 2 wherein the top disk further comprises:
   one or more of pores and undercuts for mechanical coupling with the retaining ring.

4. The access connector of claim 1 wherein the retaining ring and body are attached by chemical adhesion, mechanical attachment or a combination thereof.

5. The access connector of claim 4 wherein the body further comprises:
   one or more of pores and undercuts for mechanical coupling with the retaining ring.

6. The access connector of claim 1 wherein the retaining ring is bonded to the body by one of ultrasonic welding, solvent bonding and adhesive bonding.

7. An access connector comprising:
   a septum including a top disk, a bottom disk, and a column extending between the top disk and the bottom disk;
   a retaining ring of a different material than the septum overmolded around and integrally joined to the top disk of the septum so that mating features on the septum and the retaining ring mate and form an integral unit to prevent axial displacement and rotational movement of the septum; and
   a housing comprising a body and a base, the body including a top end having a tower and a bottom end attached to the base, the tower having a top rim attached to a bottom end of the retaining ring and forming a resealable channel with the septum for accessing a patient fluid line with a tubular portion of a medical device, wherein the bottom disk of the septum is positioned in the bottom end of the body, the column extends through the tower without contacting the tower, and the top disk is positioned above the top rim of the body.

8. The access connector of claim 7 wherein the septum includes a slit for accepting the tubular portion, and wherein the retaining ring compresses the slit shut.

9. The access connector of claim 7 wherein the top disk and retaining ring are attached by chemical adhesion, mechanical attachment or a combination thereof.

10. The access connector of claim 9 wherein the top disk is shaped to provide mechanical coupling with the retaining ring.

11. The access connector of claim 7 wherein the retaining ring is attached to a body of the housing by one or more of bonding, chemical adhesion and mechanical attachment.

* * * * *